(12) United States Patent
Mcdonell

(10) Patent No.: US 9,974,689 B2
(45) Date of Patent: May 22, 2018

(54) DUAL MODE VITRECTOMY SURGICAL SYSTEM

(71) Applicant: Novartis AG, Basel (CH)

(72) Inventor: Brian William Mcdonell, Irvine, CA (US)

(73) Assignee: Novartis AG, Basel (CH)

( * ) Notice: Subject to any disclaimer, the term of this patent is extended or adjusted under 35 U.S.C. 154(b) by 574 days.

(21) Appl. No.: 14/534,361

(22) Filed: Nov. 6, 2014

(65) Prior Publication Data
US 2016/0128870 A1 May 12, 2016

(51) Int. Cl.
*A61F 9/007* (2006.01)
*A61B 17/00* (2006.01)

(52) U.S. Cl.
CPC .......... *A61F 9/00763* (2013.01); *A61B 17/00* (2013.01); *A61B 2017/00539* (2013.01)

(58) Field of Classification Search
CPC .. A61F 9/007; A61F 9/00709; A61F 9/00736; A61F 9/00763; A61B 2017/00539; A61B 2017/00544; A61B 17/32002; A61B 17/3205; A61B 17/32053; A61B 2017/00535; A61B 2017/320028; A61B 2017/320032; A61B 10/02; A61B 10/0233; A61B 10/04; A61B 2010/0208; A61B 2010/0225
See application file for complete search history.

(56) References Cited

U.S. PATENT DOCUMENTS

| | | |
|---|---|---|
| 5,257,988 A | 11/1993 | L'Esperance, Jr. |
| 6,258,111 B1 | 7/2001 | Ross et al. |
| 6,383,203 B1 * | 5/2002 | Makihara ............ A61F 9/00763 604/22 |
| 6,773,445 B2 | 8/2004 | Finlay et al. |
| 6,780,165 B2 | 8/2004 | Kadziauskas et al. |
| 6,939,317 B2 | 9/2005 | Zacharias |
| 7,600,405 B2 | 10/2009 | Maurer, Jr. et al. |
| 7,938,120 B2 | 5/2011 | Kadziauskas et al. |
| 7,945,341 B2 | 5/2011 | Boukhny et al. |
| 8,048,094 B2 | 11/2011 | Finlay et al. |
| 8,080,029 B2 | 12/2011 | Charles |
| 8,172,865 B2 | 5/2012 | DeBoer et al. |

(Continued)

FOREIGN PATENT DOCUMENTS

| | | |
|---|---|---|
| WO | 2014099982 A1 | 6/2014 |
| WO | 2014099993 A1 | 6/2014 |
| WO | 2016073194 A1 | 5/2016 |

OTHER PUBLICATIONS

Wikipedia, Slide Valve, http://en.wikipedia.org/wiki/Slide_valve downloaded Oct. 27, 2014.

(Continued)

*Primary Examiner* — Ryan J Severson
*Assistant Examiner* — Christian Knauss

(57) ABSTRACT

An ophthalmic surgical probe for treating an eye of a patient includes a body, a cutting element extending distally from the body (the cutting element having a sleeve member with a port at an end), an inner member disposed within the sleeve member (the inner member being movable axially with respect to the sleeve member to open and close the port), and an actuating element secured to the inner member (the actuating member configured for operation in both a resonant mode and a non-resonant mode).

17 Claims, 10 Drawing Sheets

(56) References Cited

U.S. PATENT DOCUMENTS

| | | |
|---|---|---|
| 8,298,253 B2 | 10/2012 | Charles |
| 8,312,800 B2 | 11/2012 | Turner et al. |
| 2005/0054971 A1 | 3/2005 | Steen et al. |
| 2006/0114175 A1 | 6/2006 | Boukhny |
| 2007/0078379 A1 | 4/2007 | Boukhny et al. |
| 2007/0156129 A1 | 7/2007 | Kovalcheck |
| 2009/0082715 A1 | 3/2009 | Charles |
| 2014/0171995 A1 | 6/2014 | McDonell |
| 2014/0171996 A1 | 6/2014 | McDonell et al. |
| 2014/0296900 A1 | 10/2014 | Barnes et al. |

OTHER PUBLICATIONS

Youtube, Snapshots from YouTube Video at https://www.youtube.com/watch?v=vYSJn0U0kXI&feature=youtube_gdata_player, publication date Oct. 19, 2012.

* cited by examiner

DUAL MODE VITRECTOMY SURGICAL SYSTEM

FIELD OF THE INVENTION

The present disclosure relates to apparatuses and methods for ophthalmic medical procedures, and more particularly, to apparatuses and methods including vitreous fluid extraction.

BACKGROUND

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibrils that are often attached to the retina. Therefore, cutting and removal of the vitreous must be done with great care to avoid traction on the retina, the separation of the retina from the choroid, a retinal tear, or, in the worst case, cutting and removal of the retina itself. Delicate operations such as mobile tissue management (e.g., cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Standard vitrectomy probes typically include a hollow needle with a port on the end to pull in vitreous fibrils. An inner member, placed within the hollow needle, moves back and forth to open and close the port. This operates to cut any fibrils that enter the port while it is open. The rate at which the inner member moves with respect to the hollow needle is referred to as the cut rate. In some cases it is desirable to have a high cut rate. But, in some cases, it is desirable to have a relatively low, but more precise, cut rate. In some cases, it may even be desirable to perform a single cut. There is a need for continued improvement in the use and operability of vitrectomy probes. The systems discussed herein are arranged to address one or more of the deficiencies in the prior art.

SUMMARY

This disclosure relates generally to, and encompasses, apparatuses and methods for removing fluid from the eye, and more specifically to ophthalmic surgical systems and methods of using the systems to remove fluid from the eye.

An ophthalmic surgical system for treating an eye of a patient includes a body and a cutting element extending distally from the body. The cutting element includes a sleeve member comprising a port at an end. The cutting element also includes an inner member disposed within the sleeve member, the inner member being movable axially with respect to the sleeve member to open and close the port. The cutting element also includes an actuating element secured to the inner member, the actuating element configured for operation in both a resonant mode and a non-resonant mode. Operation in the resonant mode causes reciprocal movement of the inner member under application of a constant supply of pressurized fluid and operation in the non-resonant mode causes movement of the inner member in accordance with a pulse of pressurized fluid.

An ophthalmic surgical system includes a probe. The probe includes a body and a cutting element extending distally from the body. The cutting element includes a sleeve member comprising a port at an end. The cutting element also includes an inner member disposed within the sleeve member. The cutting element also includes an actuating element configured to move the inner member axially with respect to the sleeve member to open and close the port. The actuating element includes a chamber, a diaphragm that is movable within the chamber, and a flow director cooperatively associated with the inner member such that movement of the inner member causes a delayed switching of the switch valve. The system also includes a console comprising a pressurized fluid source in fluid communication with the probe.

A method of using a vitrectomy probe includes operating in a resonant mode by applying a pressurized fluid that is pressurized above a threshold value to an actuating element of the vitrectomy probe. The actuating element reciprocally actuates an inner member of a cutting element with respect to a sleeve member of the cutting element. The inner member is positioned within the sleeve member. The sleeve member extends distally from a body of a probe. The sleeve member comprises a port positioned such that actuating the inner member opens and closes the port. The method further includes operating in a non-resonant mode by applying a controlled, pressurized fluid below the threshold value to cause at least one single cycle of movement of the inner member with respect to the sleeve member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
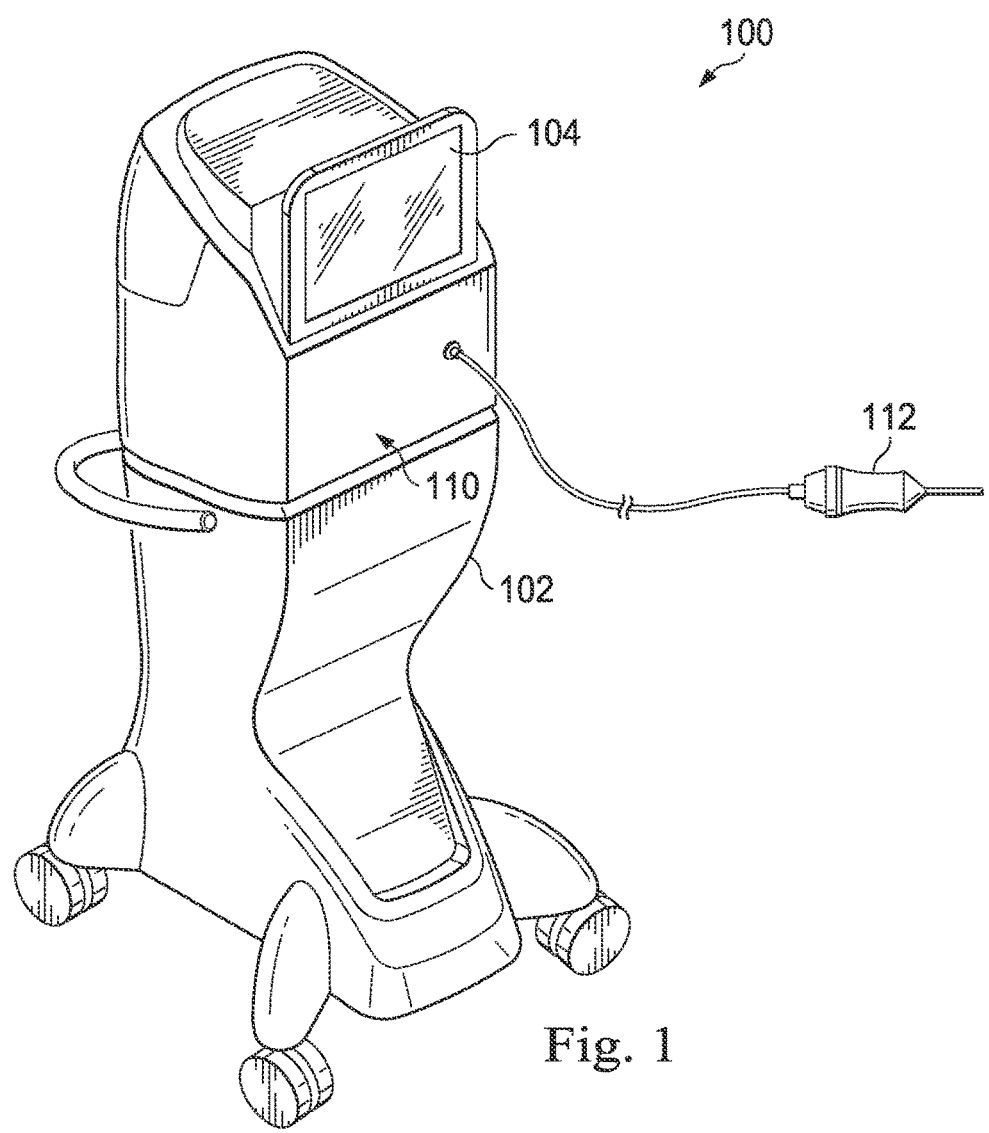
FIG. 1 is a diagram showing an illustrative vitrectomy surgical system according to one example incorporating the principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for removing ocular tissue and/or fluid from the eye. The various figures show embodiments of exemplary ophthalmic surgical probes and methods of using the probes to remove ocular tissue and/or fluid from a patient's eye. Some embodiments described herein incorporate a dual mode vitrectomy probe that can operate in either a high cut-rate resonant mode or a low cut-rate or single cut non-resonant mode. One of ordinary skill in the art, however, would understand that similar embodiments could be used to remove tissue and/or fluid from other locations in the body without departing from the general intent or teachings of the present disclosure.

FIG. 1 is a diagram showing an illustrative vitrectomy surgical system 100. According to the present example, the vitrectomy surgical system 100 includes a base housing 102 and an associated display screen 104 showing data relating to system operation and performance during a vitrectomy surgical procedure. In this exemplary embodiment, the vitrectomy surgical system 100 includes a mobile console 110 that may be used by a health care provider to perform a vitrectomy surgical procedure. The vitrectomy surgical system 100 includes a dual mode vitrectomy probe 112 and is configured to be used during an ophthalmic surgical procedure, such as, for example, a vitrectomy surgical procedure. The base housing 102 may be configured to process, receive, and store data and provide signals to the vitrectomy probe and/or the display 104.

Figure 2:
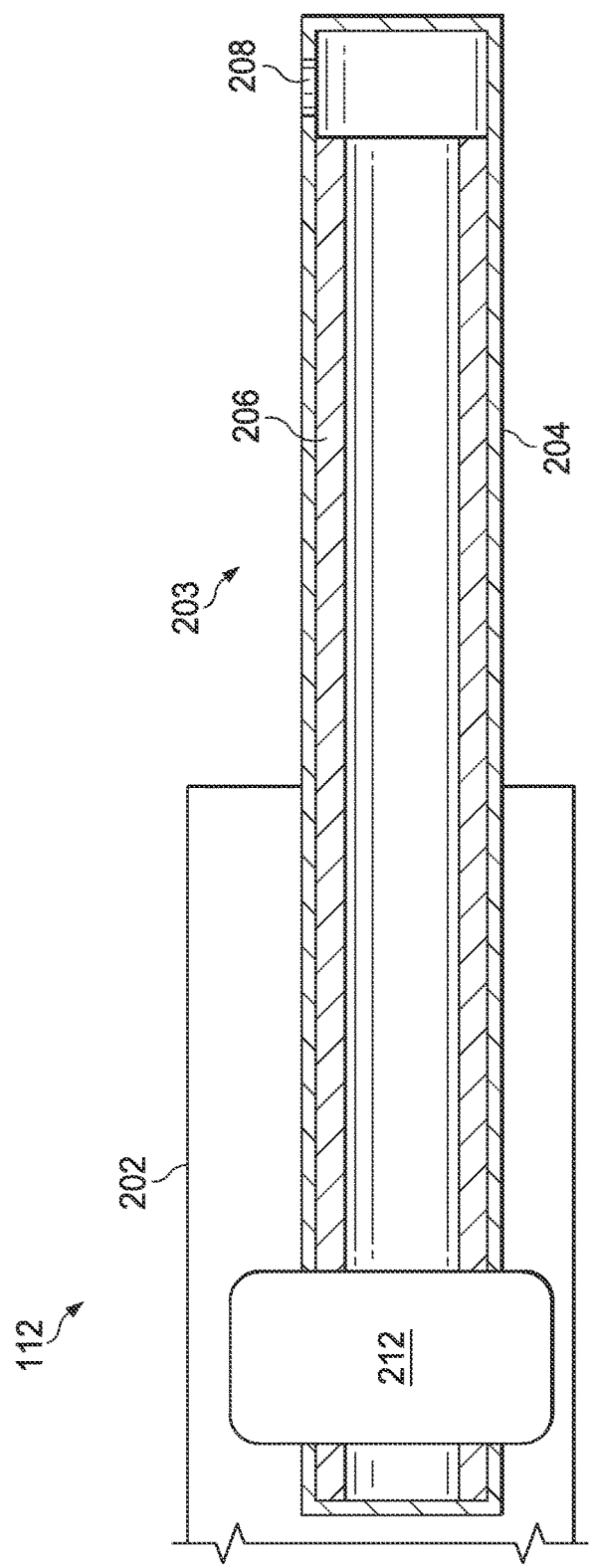
FIG. 2 is a diagram showing an illustrative longitudinal cross-sectional view of a portion of dual mode vitrectomy probe according to one example incorporating the principles described herein.

FIG. 2 is a stylized diagram showing a portion of the illustrative dual mode vitrectomy probe 112. FIG. 2 shows a longitudinal cross-sectional view of the vitrectomy probe 112. According to the present example, the vitrectomy probe 112 includes a body 202, which is shown in part. The body 202 supports a cutting element 203 that includes a sleeve member 204, an inner member 206, and an actuating element 212.

The body 202 may be made from a variety of materials commonly used to form such tools. For example, the body 202 may be made of a lightweight aluminum, plastic, or other material. The exterior portion of the body 202 may be ergonomically designed for comfortable grasping by a surgeon or operator of the vitrectomy probe 112. The inner portion of the body 202 is designed to support the cutting element 203 and other features that may be included with the probe 112.

The cutting element 203 includes the inner member 206 and the sleeve member 204. The sleeve member 204 is a hollow needle designed to enter a patient's eye. The sleeve member 204 includes a port 208 at the distal end. The port 208 is disposed along the side of the distal end as illustrated. The port 208 may be a square, rectangular, circular, elliptical, or other shaped opening. The opening is designed to allow vitreous fibrils from the patient's eye to enter. Movement of the inner member 206 within the sleeve member 204 operates to open and close the port 208, thereby cutting any vitreous fibrils that enter the port 208 while it is open.

The inner member 206 of the cutting element 203 is a hollow tube that operates as the cutter portion of the vitrectomy probe 112. Thus, the distal end of the inner member 206 is sufficiently sharp to cut vitreous fibrils. The inner member 206 may be made from a variety of materials, including for example, stainless steel and others. In some cases, the inner member 206 may include multiple members attached together. For example, the distal end of the inner member 206 may be a cutter member made of a different material than the proximal end. The proximal end of the inner member 206 may be connected to an actuating element 212 that moves the inner member 206 with respect to the sleeve member 204.

The actuating element 212 is designed to move the inner member 206 with respect to sleeve member 204 in one of a plurality of modes. Specifically, the actuating element 212 may operate in a resonant mode. In the resonant mode, a constant pressurized fluid is supplied to the probe 112. The actuating element 212 then moves at a very high rate under application of such pressurized fluid. The actuating element 212 may also operate in a non-resonant mode. In the non-resonant mode, controlled pulses of pressurized fluid are supplied to the probe 112. In some examples, a single pulse causes a single cut. In some examples, a series of pulses is used to operate the probe 112 at a low cut-rate.

Figure 3A:
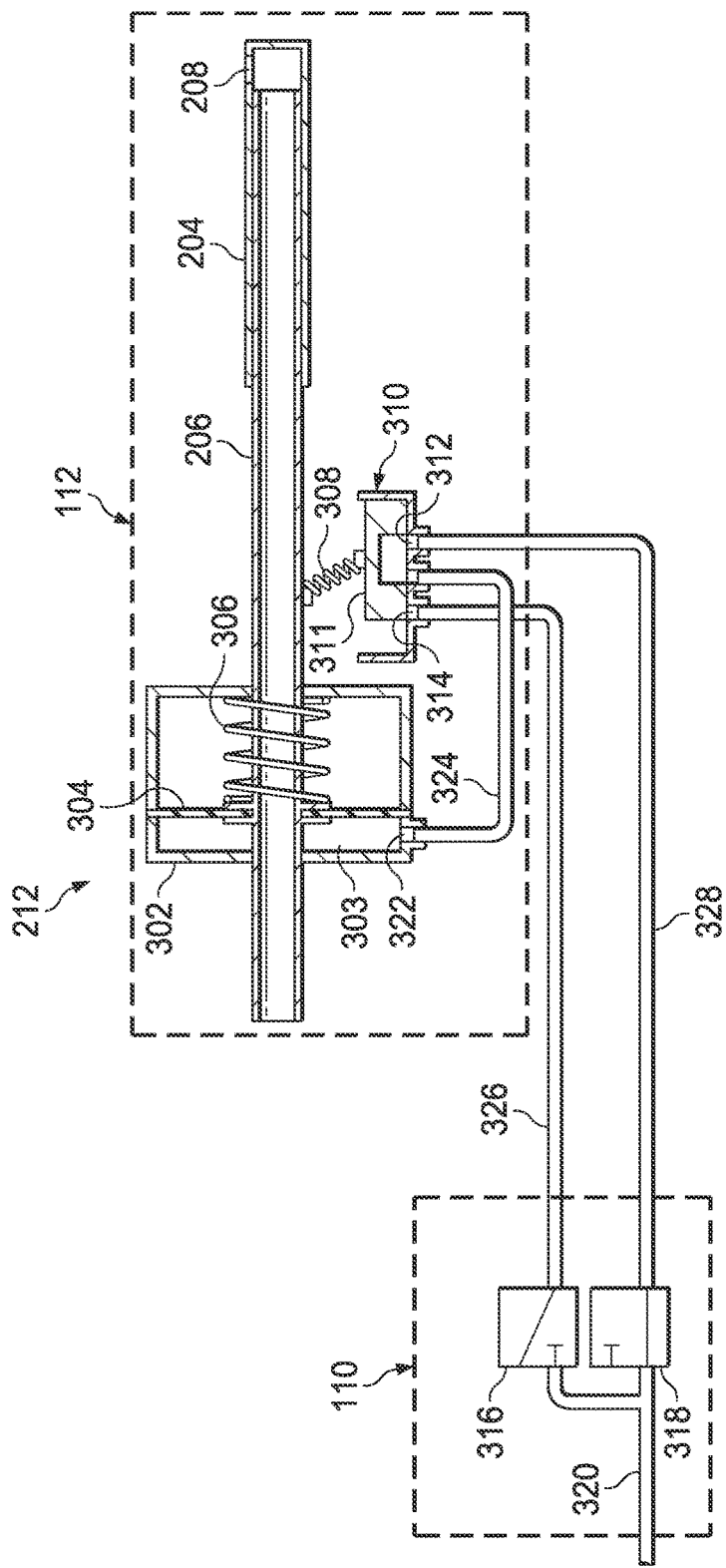
FIGS. 3A and 3B are diagrams showing an illustrative dual mode vitrectomy probe in a resonant mode according to one example incorporating the principles described herein.
Figure 3B:
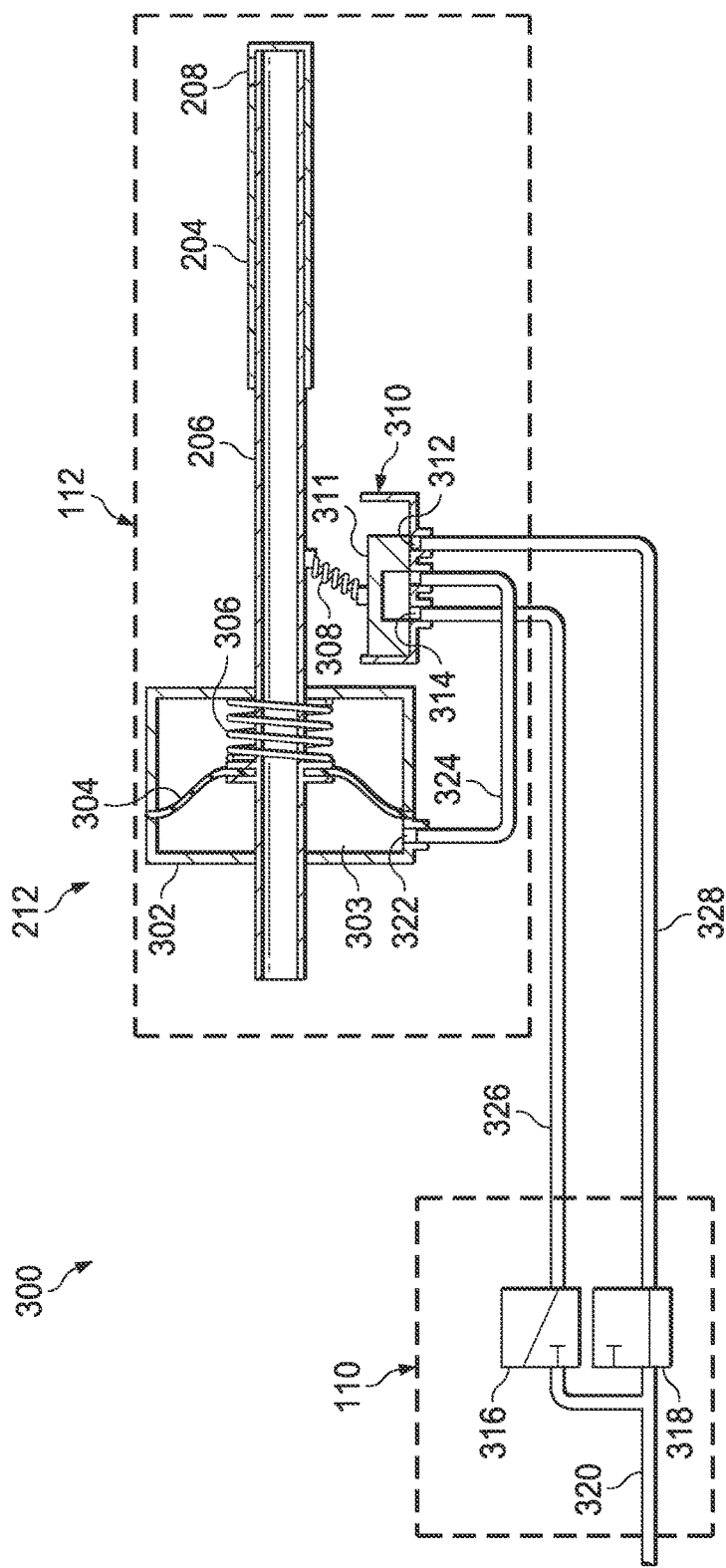

FIGS. 3A and 3B are diagrams showing an illustrative dual mode vitrectomy probe 112 in a resonant mode. According to the present example, the probe 112 includes an actuating element 212 that includes a spring loaded diaphragm 304 within a chamber 302. The chamber 302 is in fluid connection with a flow director such as a slide valve 310. The slide valve 310 is in fluid communication with two switch valves 316, 318. The configuration of the switch valves 316, 318 can be used to determine how pressurized fluid is applied to the probe, and thus, the mode in which the probe 112 operates.

In one example, the chamber 302 is a cylindrical chamber having holes at each end through which the inner member 206 can pass. The chamber 302 may be secured to the internal body of the probe 112, thereby fixing the chamber 302 in place. The chamber 302 is not secured to the inner member 206, and thus the inner member 206 can move with respect to the chamber 302. The chamber 302 also includes a proximal section 303 that can be filled with a fluid. The fluid may also be vented out of the proximal section 303.

The chamber 302 includes the diaphragm 304 that is movable within the chamber 302. The diaphragm 304 is secured to the inner member 206 such that movement of the diaphragm 304 causes respective movement of the inner member 206. In some embodiments, the diaphragm 304 may be disc shaped to fit within the cylindrical chamber 302 and form a seal around the circumferential edges of the diaphragm 304. Other shapes for the chamber 302 and diaphragm 304 are contemplated.

The diaphragm 304 is connected to the distal end of the chamber 302 through a biasing element 306 such as a spring mechanism 306. The biasing element 306 places a force on the diaphragm 304 in the proximal direction. Thus, pressurized fluid entering the chamber will cause the diaphragm 304 to move against the spring force, thus causing the inner member 206 to move in a distal direction and close the port 208. When the fluid within the proximal section 303 is no longer pressurized, the spring force from the biasing element 306 will push the fluid back out of the chamber 302, thus moving the inner member 206 in a proximal direction to open the port 208.

Fluid enters the chamber 302 through a port 322. The port 322 is in fluid communication with a slide valve 310. In this embodiment, the slide valve 310 moves between one of two positions. In the first position, as illustrated in FIG. 3A, path 312 is open and path 314 is closed. In the second position, which is illustrated in FIG. 3B, path 312 is closed and path 314 is open.

The slide valve 310 acts as a flow director because it directs the flow of fluid between the chamber 302 and the console switch valves 316, 318. Specifically, the flow directing slide valve 310 switches to direct the flow into or out of the chamber 302. According to the present example, the slide valve 310 includes a slider 311 that moves between two positions. The slider 311 is secured to the inner member 206 such that movement of the inner member 206 causes a delayed switching of the slide valve 310. For example, the slider 311 of the slide valve 310 may be connected to the inner member 206 through a spring mechanism 308.

In the present example, the spring mechanism 308 is always under compression, and thus pushes the slider 311 to an opposite position of the inner member 206. For example, while the inner member 206 is in the proximal position, the spring mechanism 308 pushes the slider 311 into the distal position as illustrated in FIG. 3A. As the inner member 206 moves from the proximal position to the distal position, it will eventually pass a center point at which the spring mechanism 308 will then push the slider into the proximal position as illustrated in FIG. 3B. Thus, the slider 311 will tend to be in the opposite position of the inner member 206. As will be described in further detail below, this provides some hysteresis to the system, thus allowing for the resonant nature of the actuating element 212.

The console 110 includes a pressurized fluid supply 320 that is provided to two console switch valves 316, 318. The console switch valves 316, 318 may be in either a supply mode or a vent mode. In supply mode, the pressurized fluid from the fluid supply 320 is passed through the switch valves 316, 318. In vent mode, the fluid supply 320 is disconnected and any fluid from the probe 112 may be vented through the console switch valves 316, 318. Switch valve 316 is connected to path 314 of the slide valve 310 through line 326. Switch valve 318 is connected to path 312 of the switch valve 310 through line 328.

FIG. 3A illustrates stage 1 of the resonant mode. While in resonant mode, console switch valve 316 is in vent mode, and console switch valve 318 is in supply mode. Additionally, a constant supply of pressurized fluid is provided through the pressurized fluid supply 320. Thus, pressurized fluid passes through console switch valve 318, line 328, path 312, line 324, and into the proximal section 303 of the chamber 302 through port 322. As the proximal section 303 of the chamber 302 fills up with pressurized fluid, the diaphragm 304 is pushed in a distal direction, thus moving the inner member 206 in the distal direction so as to close the port 208. The slider 311 of the switch valve 310 will remain in the illustrated position for a sufficient amount of time to let the chamber 302 fill up with fluid and move the inner member 206. Eventually, the spring force of the spring mechanism 308 will push the slider 311 of the switch valve 310 into the second position.

FIG. 3B illustrates stage 2 of the resonant mode. When the diaphragm 304 and inner member 206 are in the distal position, the slider 311 will have been pushed to the second position. With the slider 311 in the second position, the pressurized fluid within the chamber 302 is vented out of the port 322, back through line 324, through path 314, through line 326, and vented out of console switch valve 316. As the pressurized fluid is vented out of the chamber 302, a biasing force, such as a spring force from the biasing element 306 pushes the diaphragm 304 and the inner member 306 back into the proximal position. After the chamber is sufficiently vented to allow the inner member to move proximally, the force of spring 308 will move the slider 311 back to the first position, wherein the cycle starts again as pressurized fluid from the pressurized fluid supply 320 is pumped through console switch valve 318 and eventually into the chamber 302. The resonant mode may be particularly useful when high cut-rates, such as cut-rates exceeding 7,500 cuts per minute, are desired.

Figure 4:
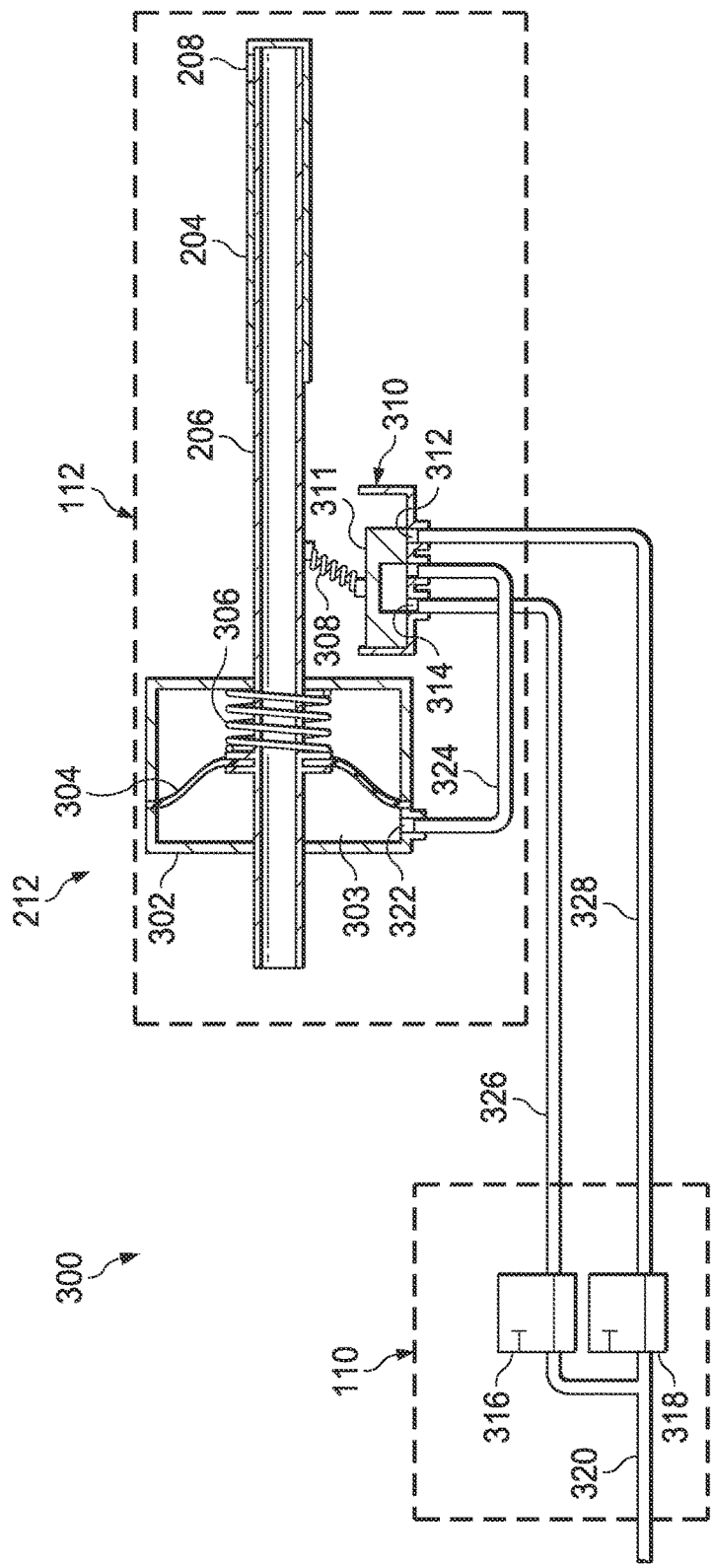
FIG. 4 is a diagram showing an illustrative dual mode vitrectomy probe in a non-resonant mode according to one example incorporating the principles described herein.

FIG. 4 is a diagram showing the illustrative dual mode vitrectomy probe in a non-resonant mode. According to the present example, in the non-resonant mode, a single cut or a low cut-rate may be performed as described below. To perform a single cut, both console switch valves are set in supply mode. Then, pressurized fluid is supplied through both console switch valves 316, 318 at the same time. In some cases, pressurized fluid may be supplied through console switch valve 316 slightly before being applied to console switch valve 318. That is, console switch valve 316 may be opened slightly before console switch valve 318. The pressurized fluid will fill up the chamber 302 to cause the diaphragm 304 and the inner member 206 to move into the distal position. The spring mechanism 308 eventually responds to the movement of the inner member 206, thereby causing the slider 311 to move into the second position. But, because pressure is being applied through both console switch valves 316, 318, the pressure will be maintained within the chamber 302 to keep the inner member 206 in the distal position until the pressure is relieved. Pressure may be relieved by switching the console switch valves 316, 318 to the vent position. This will allow any fluid within the chamber 302 to be vented out. Alternatively, pressure may be relieved by discontinuing pressure through the pressurized fluid supply 320.

To operate the probe 112 at a low cut-rate, the console 110 can apply a series of pulses of pressurized fluid through the console switch valves 316, 318. Each pulse will cause a single cut as described above. The rate at which the probe 112 operates in non-resonant mode is controlled by adjusting the nature of the pulses of pressurized fluid being supplied through the console switch valves 316, 318.

In some embodiments, such as the embodiment disclosed in FIGS. 3A, 3B, and 4, the mode is changed via operation of the console switch valves 316, 318. In accordance with this embodiment, the console 110 may include a mode selector input, such as a button, dial, or switch, for example, to enable the system to switch between modes. In some examples, the console operates to automatically select the operational mode based on a selected cut rate, with the console automatically operating in the resonant mode when the cut-rate is set above a threshold and automatically operating in the non-resonant mode when the cut-rate is below a threshold. In some embodiments the mode is determined by the pressure of the fluid being supplied to the probe.

Figure 5:
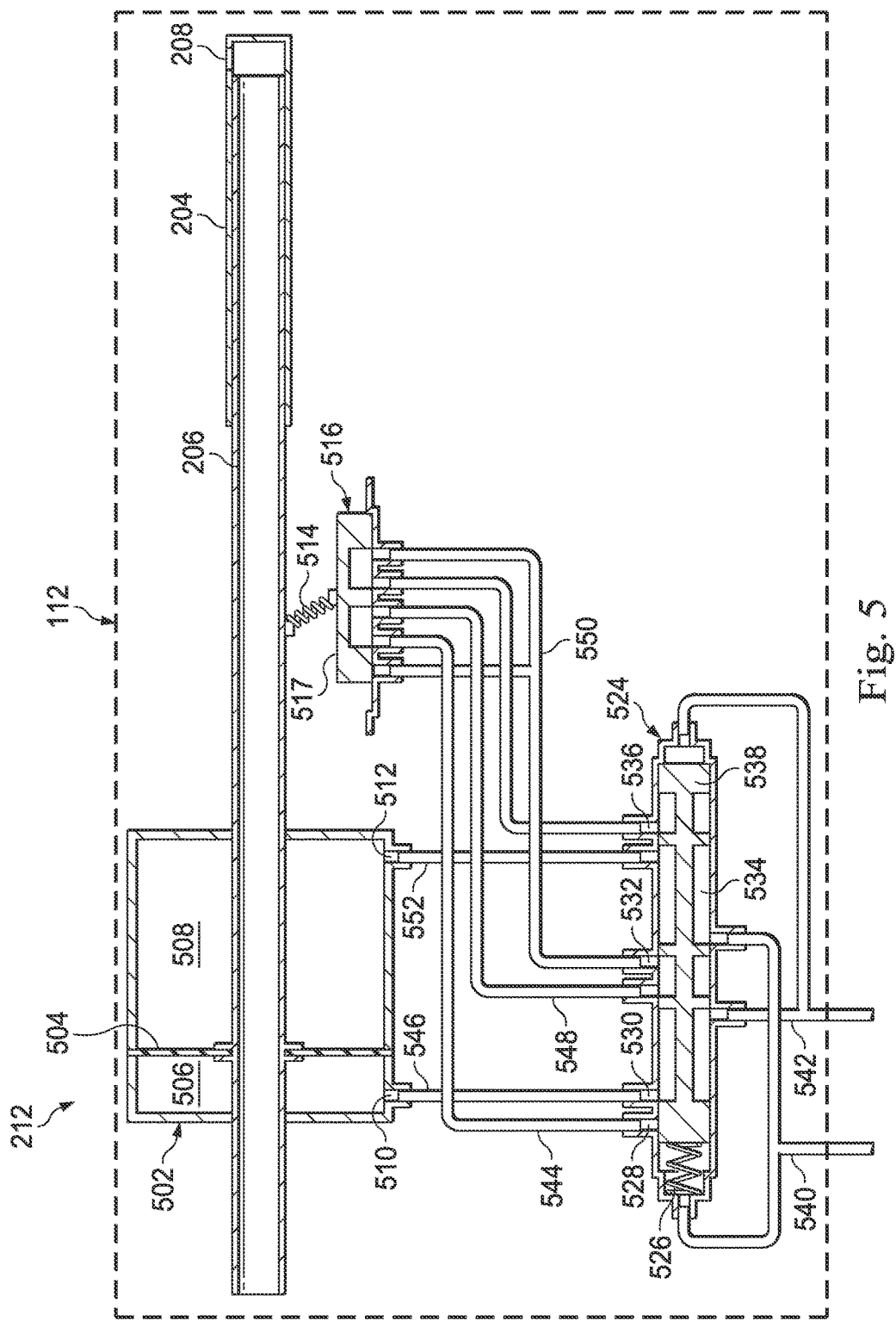
FIG. 5 is a diagram showing an illustrative dual mode vitrectomy probe in a non-resonant mode according to one example incorporating the principles described herein.

FIG. 5 is a diagram showing an illustrative dual mode vitrectomy probe 112 when the system is operating in a non-resonant mode. According to the present example, the probe 112, includes an actuating element 212 having a chamber 502 that has a proximal section 506 and a distal section 508 separated by a diaphragm 504. The sections 506, 508 are in fluid connection with a control valve system that forms a part of the probe 112. In one example, the control valve system is a spool valve 524. The spool valve 524 is in fluid connection with fluid director such as switch valve 516. The spool valve 524 is used to switch the probe 112 between a resonant mode and a non-resonant mode. The spool valve 524 is also in fluid connection with fluid supply lines that connect between the probe 112 and a console (not shown), such as console 110.

The chamber 502 is divided into the proximal section 506 and the distal section 508. The diaphragm 504 may be disc-shaped to form a seal with the inner wall of the chamber 502 so as to seal the distal section 508 from the proximal section 506. The diaphragm is secured to the inner member 206 such that movement of the diaphragm 504 causes movement of the inner member 206. Pumping a fluid into the proximal section 506 increases the volume of the proximal section 506 and decreases the volume of the distal section 508 by pushing fluid out of the distal section 508. Conversely, pumping fluid into the distal section 508 increases the volume of the distal section and decreases the volume of the proximal section 506 by pressing fluid out of the proximal section 506.

The spool valve 524 includes a spool 538 that is movable between two positions. As illustrated in FIG. 5, the spool 538 is biased into a first position by a biasing element 526 such as a spring mechanism. The first position is such that fluid from the fluid supply lines 540, 542 bypasses the switch valve 516 and flows directly into the proximal section 506 and the distal section 508.

While in non-resonant mode, the probe 112 operates as follows. A controlled amount of pressurized fluid is applied at the console 110 to both fluid supply lines 540, 542. The pressure differential between the two fluid supplies 540, 542 is kept below a threshold level in order to keep the spool valve 524 in the first position, as illustrated in FIG. 5. Pressure pulses are alternatingly applied between fluid supply 540 and fluid supply 542. Specifically, to move the inner member 206 and close the port 208, a pressure pulse is applied through fluid supply 542. This fluid pulse passes through path 530 of the spool valve 524, through line 546, through port 510 and into the proximal section 506 of the chamber 502. The fluid pulse is sufficient to move the diaphragm 504 and press any fluid within the distal section 508 out of port 512, through line 552, through path 534 of the spool valve 524 and back through fluid supply line 540.

To move the inner member 206 and open the port 208, a fluid pulse is applied at fluid supply 540. This fluid pulse passes through path 534 of the spool valve 524, through line 552, through port 512 and into the distal section 508 of the chamber 502. The fluid pulse is sufficient to move the diaphragm 504 in the distal direction, thereby pressing fluid out of the proximal section 506. Any fluid within the proximal section 506 is then pressed out of port 510, through line 546, through path 530 of the spool valve 524, and back through fluid supply 542. Thus, by applying controlled, alternating pulses between the fluid supplies 540, 542, the probe can operate at a low cut-rate and even perform single cuts.

Figure 6A:
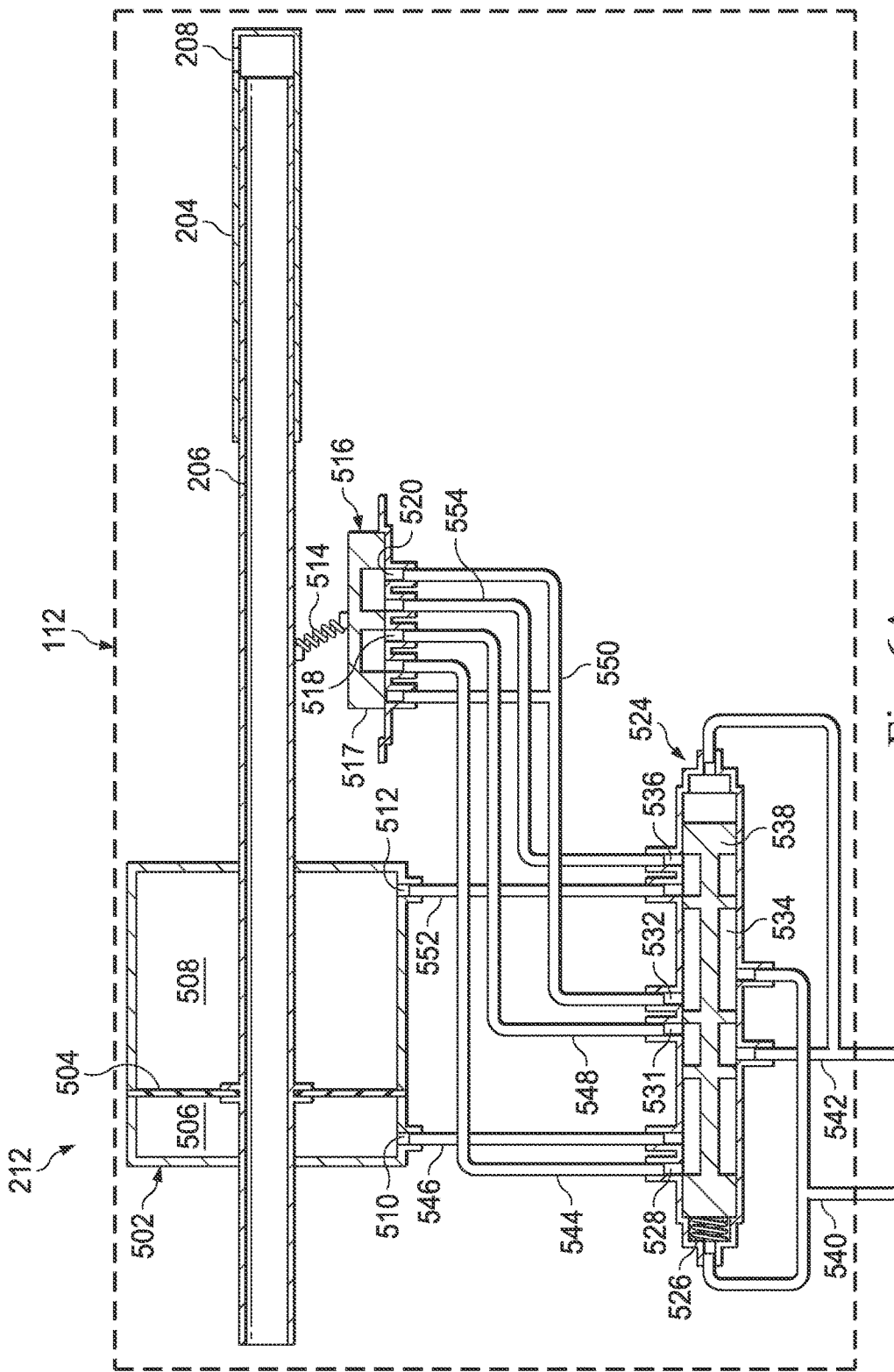
FIGS. 6A and 6B are diagrams showing an illustrative dual mode vitrectomy probe in a resonant mode according to one example incorporating the principles described herein.
Figure 6B:
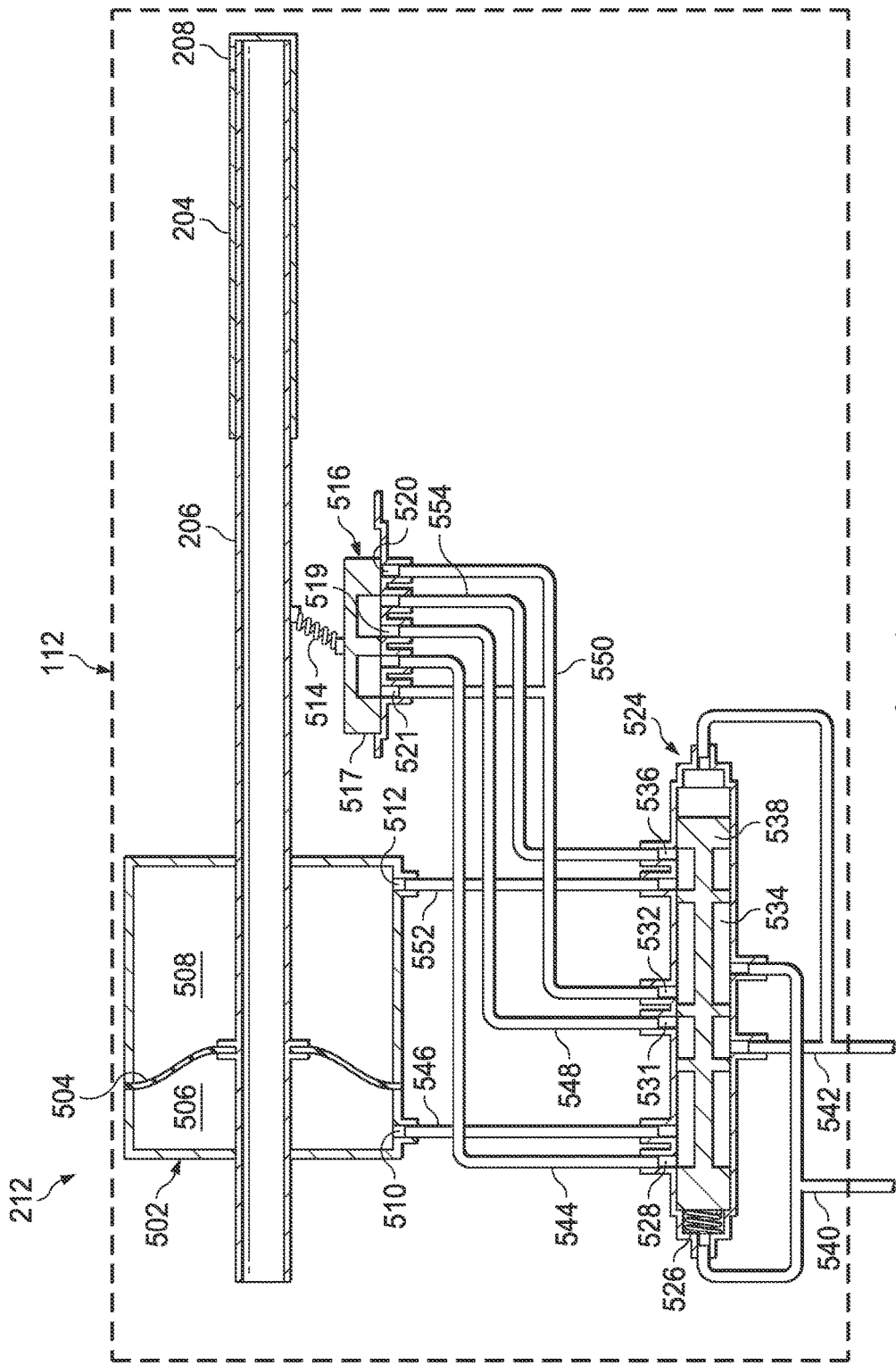

FIGS. 6A and 6B are diagrams showing an illustrative dual mode vitrectomy probe 112 in a resonant mode. FIG. 6A illustrates stage 1 and FIG. 6B illustrates stage 2 of the resonant mode. To put the probe in a resonant mode, the pressure differential between the fluid supplies 540, 542 exceeds a threshold level. Specifically, the pressure at fluid supply 542 is sufficiently greater than the pressure at fluid supply 540 such that the spring force of the biasing element 526 is overcome. This moves the spool 538 into a second position as illustrated in FIGS. 6A and 6B.

With the spool 538 in the second position, fluid from fluid supply 542 will pass through path 531 of the spool valve 524, through line 548, through path 518 of the slide valve 516, through line 544, through path 528 of the spool valve 524, through line 546, through port 510, and into the proximal chamber 506. This will move the diaphragm 504 and the inner member 206 so as to close the port 208. This will also press any fluid within the distal chamber 508 out of port 512, through line 552, through path 536 of the spool valve 524, through line 554, through path 520 of the switch valve 516, through line 550, through path 532 of the spool valve 524, and out of supply line 540.

The slide valve 516 acts as a flow director by directing flow either into or out of either section 506, 508. In one example, the slide valve 516 includes a slider 517. The slider 517 is connected to the inner member 206 with a compressed spring mechanism 514 such that movement of the inner member 206 causes a delayed movement of the slider 517. When the slider 517 changes position, as shown in FIG. 6B, the pressurized fluid from fluid supply 542 is rerouted so as to fill up the distal section 508 instead of the proximal section 506. Specifically, fluid from fluid supply 542 passes through path 531, through line 548, through path 519 of the slider valve 516, through line 554, through path 536 of the spool valve 524, through line 552, through port 512, and into the distal section 508. This moves the diaphragm 504 and the inner member 206 into the proximal position so as to open the port 208. This also presses fluid out of the proximal section 506 through the port 510, through line 546, through path 528, through line 544, through path 521 of the slide valve 516, through line 550, through path 532 of the spool valve 524, and out of fluid supply 540. Movement of the inner member 206 will eventually cause movement of the slider 517, which will again reroute the fluid from fluid supply 542 to the proximal section 506, thereby repeating the cycle.

While the present embodiment utilizes a spool valve 524, other types of valves that can switch fluid pathways are contemplated. Additionally, the slide valve 516 may be one of a variety of valves that are able to switch fluid pathways, including a spool valve.

While the embodiments described above and illustrated in the corresponding figures relate to a probe that cuts fibers by opening and closing the ports, it is understood that principles described herein may be applied to other types of cutters as well. In some examples, motion of an inner member does not open and close the port. Rather, motion of the inner member moves a cutter that moves across the port to cut tissue but does not actually open or close the port.

Figure 7A:
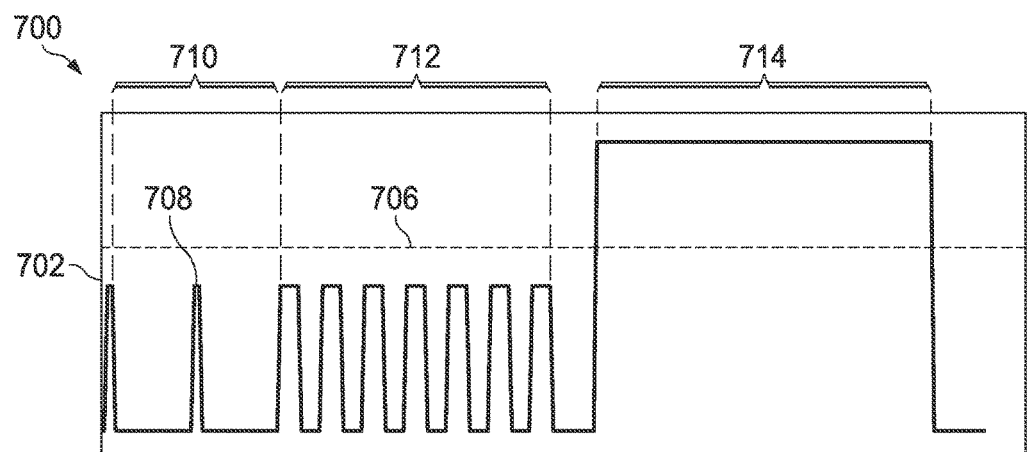
FIG. 7A is a graph showing a relationship between applied pressure and probe cut-rate according to one example incorporating the principles described herein.

FIG. 7A is a graph 700 showing a relationship between applied pressure and probe cut-rate. The vertical axis 702 of the graph represents pressure. The horizontal axis 704 of the graph 700 represents time. The dotted line 706 represents a threshold pressure level.

The graph illustrates the applied pressure as a function of time. In the first mode 710, single cuts are made by applying a single pulse of pressure. The single cut may be initiated by a control mechanism associated with the console, or may be initiated by a control mechanism on the hand-piece of the probe. In some examples, a foot pedal may be connected to the console, that when pressed by an operator of the probe, causes a single pulse to be delivered to the probe. The single pulse of fluid causes the probe to perform a single cut.

In the second mode 712, the console causes a series of pulses to be applied to the probe to operate the probe at a low cut-rate. For example, the low cut-rate may range from 500 to 5,000 cuts per minute. The probe 112 may be set to operate in the low cut-rate mode 712 through a control mechanism associated with the console.

When using the probe 112 in the single cut mode 710 or the low cut-rate mode 712, the pressure associated with the pulses is less than a threshold level. The threshold level is the level that when exceeded, causes the probe to operate in resonant mode. For example, in the embodiment described above in relation to FIGS. 5, 6A, and 6B, applying pressure higher than the threshold level causes the spool valve 524 to switch positions, thus putting the probe 112 into resonant mode 714. In one example, the speed at which the probe operates in resonant mode is substantially higher than the speed at which the probe operates in the low cut-rate mode. For example, the resonant mode 714 may involve a speed within a range of about 7,500 to 50,000 cuts per minute.

Figure 7B:
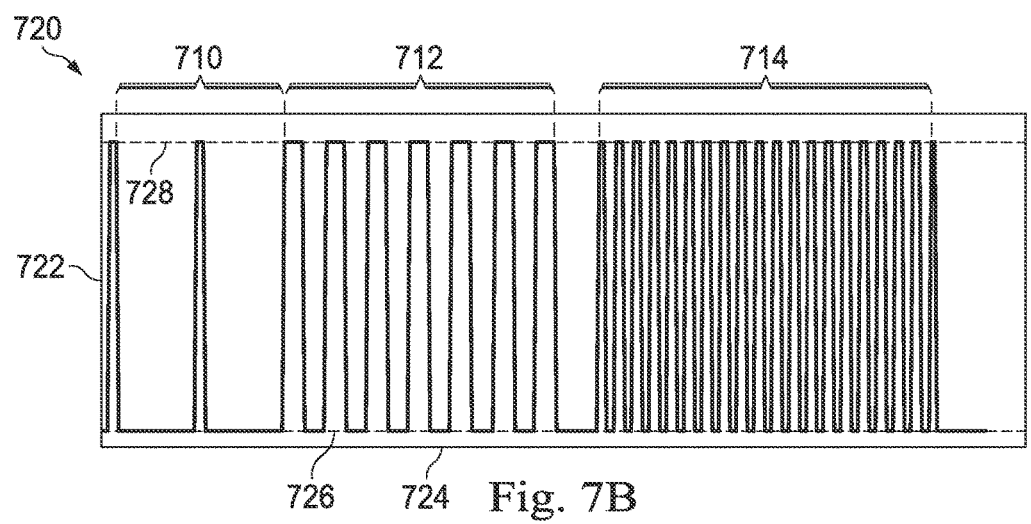
FIG. 7B is a graph showing the position of the inner member of the probe in accordance with the graph of FIG. 7A according to one example incorporating the principles described herein.

FIG. 7B is a graph 720 showing the position of the inner member 206 of the probe in accordance with the graph of FIG. 7A. The vertical axis 722 represents the position of the inner member 206. The horizontal axis 724 represents time and corresponds with the time in the horizontal axis of FIG. 7A. In this example, the inner member 206 has a default position of the proximal position 726, wherein the port 208 is open. When a pulse of fluid is supplied to the probe 112, the inner member 206 moves to the distal position 728, wherein the port 208 is closed. Thus, a pulse 708 of fluid corresponds with the inner member temporarily being in the distal position 728.

Figure 8:
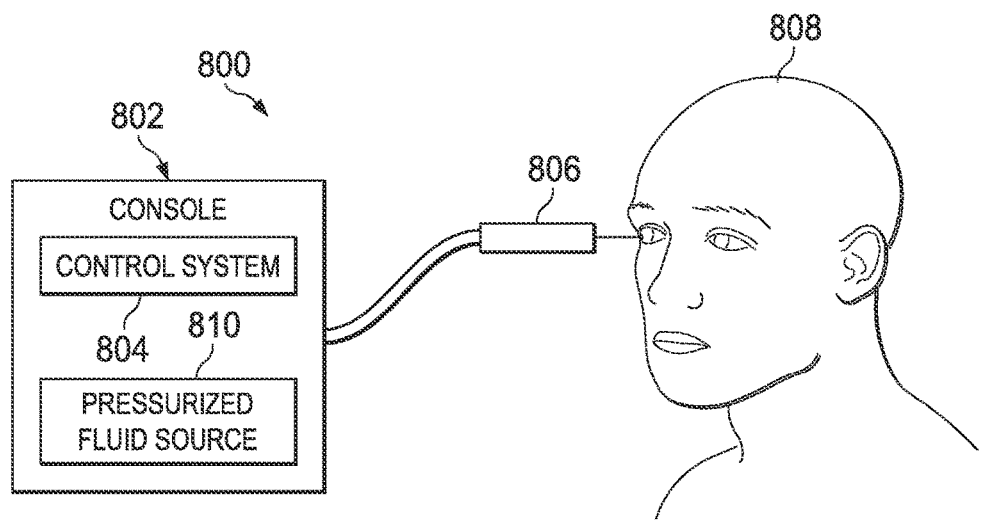
FIG. 8 is a diagram showing an ophthalmic surgical system with a dual mode vitrectomy probe performing a surgical procedure on a patient according to one example incorporating the principles described herein.

FIG. 8 is a diagram showing an ophthalmic surgical system with dual mode vitrectomy probe. According to the present example, the system 800 includes a console 802 and a hand piece 806. The console 802 includes a control system 804 and a pressurized fluid source 810. The hand piece 806 may be the same probe 112 discussed above, or may be another probe used by an operator or surgeon to treat a condition of the eye. In this example, the distal portion is inserted into the eye of a patient 808.

The console 802 includes all the necessary components to drive and work with the hand piece 806. Additional components and features of the console would be apparent to one of ordinary skill in the art. The control system 804 within the console 802 provides the desired signals to the hand piece 806 to cause the inner member to move with respect to the sleeve member and cut vitreous fibrils.

The pressurized fluid source 810 may include a chamber of fluid under pressure. The fluid may be a liquid or a gas such as atmospheric air. The pressurized fluid source may be adjusted to apply different levels of pressurized fluid to the hand piece 806. Specifically, the pressurized fluid source 810 may apply a steady pressure. Or, the pressurized fluid source 810 may apply pulses of fluid to the hand piece 806.

Figure 9:
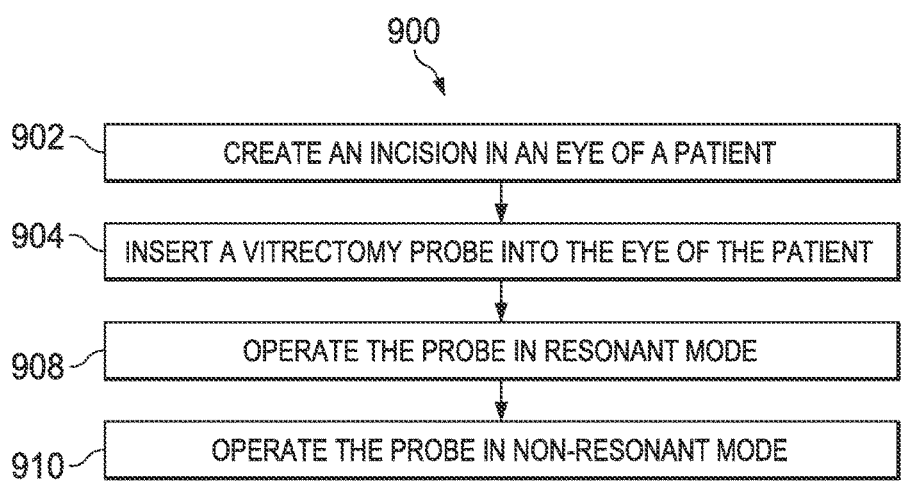
FIG. 9 is a flowchart showing an illustrative method for treating a patient with a dual mode vitrectomy probe according to one example incorporating the principles described herein.

FIG. 9 is a flowchart showing an illustrative method for treating a patient with dual mode vitrectomy probe. According to the present example, the method 900 includes creating an incision in an eye of a patient at 902. At 904, the method 900 includes inserting a vitrectomy probe into the eye of the patient.

According to some examples, the probe includes a dual mode actuating element as described above. The probe also includes a cutting element having a hollow sleeve member extending distally from the body and an inner member within the hollow sleeve member.

At 908, the method 900 includes operating the probe in a resonant mode. In the resonant mode, a constant supply of pressurized fluid is applied to the probe. The actuating element within the probe then moves back and forth under that applied pressure. For example, movement of the actuating element moves the inner member, thus opening and closing the port at the end of the hollow sleeve member.

At 910, the method 900 includes operating the probe in a non-resonant mode. In the non-resonant mode, one or more pulses of pressurized fluid are supplied to the probe to cause the probe to perform a single cut or to operate at a low cut-rate. Thus, the operator of the probe has multiple options when performing a surgical operation. Specifically, the operator may change the mode as desired to effectively remove vitreous fibrils from the eye of the patient.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An ophthalmic surgical system for treating an eye of a patient, the system comprising:
   a body;
   a cutting element extending distally from the body including:
     a sleeve member comprising a port at an end;
     an inner member disposed within the sleeve member, the inner member being movable axially with respect to the sleeve member;
   an actuating chamber comprising a diaphragm coupled to the inner member, wherein pressure changes in the actuating chamber causes the diaphragm to move resulting in movement of the inner member;
   a flow director coupled to at least two external flow lines and an internal flow line coupling the flow director to the actuating chamber; and
   an actuating element, in the flow director, secured to the inner member, the actuating element configured for operation in both a resonant mode and a non-resonant mode, wherein movement of the inner member to a distal-most position causes movement of the actuating element in the flow director from a proximal-most position to a distal-most position and wherein a change of the actuating element from the proximal-most position to the distal-most position in the flow director fluidically couples the internal flow line to a different external flow line of the at least two external flow lines than when the actuating element is in the proximal-most position;

wherein operation in the resonant mode causes reciprocal movement of the inner member under application of a constant supply of pressurized fluid and operation in the non-resonant mode causes movement of the inner member in accordance with a pulse of pressurized fluid.

2. The system of claim 1, wherein the flow director comprises a slider, the slider being connected to the inner member such that the movement of the inner member switches the slider in a delayed manner.

3. The system of claim 2, wherein the operation in the resonant mode causes movement of the slider such that fluid is reciprocally pumped and vented from the flow director.

4. The system of claim 2, wherein the operation in the non-resonant mode causes the movement of the inner member when a controlled pulse of fluid is passed through the slider such that a single cut is performed or a series of single cuts is performed.

5. The ophthalmic surgical system of claim 1, wherein the at least two external flow lines are coupled to switch valves.

6. The ophthalmic surgical system of claim 1, wherein in the resonant mode, pressure is applied through only one of the at least two external flow lines.

7. The ophthalmic surgical system of claim 1, wherein in the resonant mode, at least one external flow line vents air from the flow director.

8. The ophthalmic surgical system of claim 1, wherein the at least two external flow lines consist of two external flow lines and wherein, in the non-resonant mode, pressure is applied through both of the two external flow lines.

9. The ophthalmic surgical system of claim 1, wherein the actuating chamber comprises a spring that opposes distal movement of the diaphragm.

10. The ophthalmic surgical system of claim 1, wherein the actuating element comprises a slider and wherein the slider is configured to slide between the proximal-most position to the distal-most position.

11. The ophthalmic surgical system of claim 10, wherein the slider is directly coupled to the inner member through a spring such that the movement of the inner member causes movement of the slider.

12. The ophthalmic surgical system of claim 11, wherein the slider and the inner member move back and forth in a resonant fashion.

13. An ophthalmic surgical system comprising:
a probe comprising:
a body;
a cutting element extending distally from the body including:
a sleeve member comprising a port at an end; and
an inner member disposed within the sleeve member;
an actuating element configured to move the inner member axially with respect to the sleeve member, the actuating element comprising:
an actuating chamber;
a diaphragm, coupled to the inner member, that is movable within the chamber, wherein pressure changes in the actuating chamber causes the diaphragm to move resulting in movement of the inner member; and
a flow director cooperatively associated with the inner member such that the movement of the inner member causes a delayed switching of a slider in the flow director; and
a console comprising a pressurized fluid source in fluid communication with the probe;
wherein the flow director is coupled to at least two external flow lines and an internal flow line coupling the flow director to the actuating chamber;
wherein the slider is coupled to the inner member and wherein movement of the inner member to a distal-most position causes movement of the slider from a proximal-most position to a distal-most position and wherein the movement of the slider from the proximal-most position to the distal-most position fluidically couples the internal flow line to a different external flow line of the at least two external flow lines than when the slider is in the proximal-most position.

14. The system of claim 13, wherein the diaphragm is biased so as to force the inner member to a position wherein the port is open.

15. The system of claim 14, wherein:
while in the resonant mode, the actuating element is configured to move the inner member by passing a constant pressure through the flow director such that movement of the slider allows fluid to be reciprocally pumped and vented from the chamber; and
wherein, while in the non-resonant mode, the actuating element is configured to move the inner member by passing a controlled pressure through the flow director such that a single cut is performed or a low cut-rate is performed.

16. The system of claim 15, wherein:
the actuating element is configured to operate in the resonant mode and move the inner member when a constant pressure is passed through the flow director, the flow director being arranged so that movement of the slider allows fluid to be reciprocally pumped and vented from the chamber; and
the actuating element is configured to operate in the non-resonant mode and move the inner member when a controlled pulse of fluid is passed through the flow director, the flow director being arranged so that a single cut is performed or a series of single cuts is performed.

17. The system of claim 13, wherein the diaphragm is positioned to divide the chamber into a distal section and a proximal section, wherein both sections are in fluid communication with the console through the flow director.

* * * * *